United States Patent [19]

Sarnoff et al.

[11] Patent Number: 5,085,642
[45] Date of Patent: Feb. 4, 1992

[54] CONVENIENTLY CARRIED FREQUENT USE AUTOINJECTOR

[75] Inventors: Stanley J. Sarnoff, Bethesda; Claudio Lopez, Gaithersburg, both of Md.

[73] Assignee: Survival Technology, Inc., Bethesda, Md.

[21] Appl. No.: 380,459

[22] Filed: Jul. 17, 1989

[51] Int. Cl.⁵ .............................................. A61M 5/20
[52] U.S. Cl. ..................................... 604/134; 604/135; 604/136; 604/171; 604/220
[58] Field of Search .......... 604/95, 115, 131, 134–136, 604/138, 139, 156–157, 171, 181, 195–196, 220, 137; 401/243

[56] References Cited

U.S. PATENT DOCUMENTS

| | | | |
|---|---|---|---|
| 1,204,053 | 11/1916 | Moore | 401/243 |
| 2,565,081 | 8/1951 | Maynes | 604/136 |
| 2,832,339 | 4/1958 | Sarnoff et al. | |
| 3,380,449 | 4/1968 | Sarnoff . | |
| 3,391,695 | 7/1968 | Sarnoff . | |
| 3,396,726 | 8/1968 | Sarnoff . | |
| 3,403,679 | 10/1968 | Sinclair et al. | 604/137 |
| 3,795,061 | 3/1974 | Sarnoff et al. | |
| 3,882,863 | 5/1975 | Sarnoff et al. | |
| 3,910,260 | 10/1975 | Sarnoff et al. | |
| 4,004,577 | 1/1977 | Sarnoff . | |
| 4,031,893 | 6/1977 | Kaplan et al. | |
| 4,168,129 | 9/1979 | Herrnring | 401/243 |
| 4,316,463 | 2/1982 | Schmitz et al. | 604/135 |
| 4,380,403 | 4/1983 | Endres et al. | 401/243 |
| 4,484,910 | 11/1984 | Sarnoff et al. | 604/134 |
| 4,565,543 | 1/1986 | Bekkering et al. | 604/135 |
| 4,592,745 | 6/1986 | Rex et al. | 604/152 |
| 4,624,660 | 11/1986 | Mijers et al. | 604/136 |
| 4,661,098 | 4/1987 | Bekkering et al. | 604/135 |
| 4,689,042 | 8/1987 | Sarnoff et al. | |
| 4,755,169 | 7/1988 | Sarnoff et al. | |
| 4,795,433 | 1/1989 | Sarnoff . | |

FOREIGN PATENT DOCUMENTS 0180761 1/1955 Fed. Rep. of Germany ...... 604/192

Primary Examiner—Stephen C. Pellegrino
Assistant Examiner—Michael Rafa
Attorney, Agent, or Firm—Cushman, Darby & Cushman

[57] ABSTRACT

An autoinjector particularly suited to be carried on the person of a user comprising a housing defining an exterior configuration of a size and shape approximately the same as that of a conventional fountain pen including a housing body assembly of elongated generally cylindrical configuration and a separate housing cap structure of elongated generally cylindrical configuration having an elongated clip thereon. The housing cap structure is detachably secured to the housing body assembly in open ended telescopic relation with an opposite end portion thereof preferably by a childproof connection. A medicament cartridge assembly is mounted in a storage position within a forward end of an interior chamber within the housing body assembly and a releasable stressed spring assembly is carried by the housing body assembly adjacent the rearward end thereof. The housing cap structure serves the dual purposes of (1) facilitating the securement of the housing cap structure and body assembly with the user's pocket and (2) alleviating the likelihood of an unwanted release of the releasable stressed spring assembly with a resultant unwanted movement of the hypodermic needle of the cartridge assembly and an unwanted movement of the liquid medicament of the cartridge assembly outwardly of the needle.

20 Claims, 2 Drawing Sheets

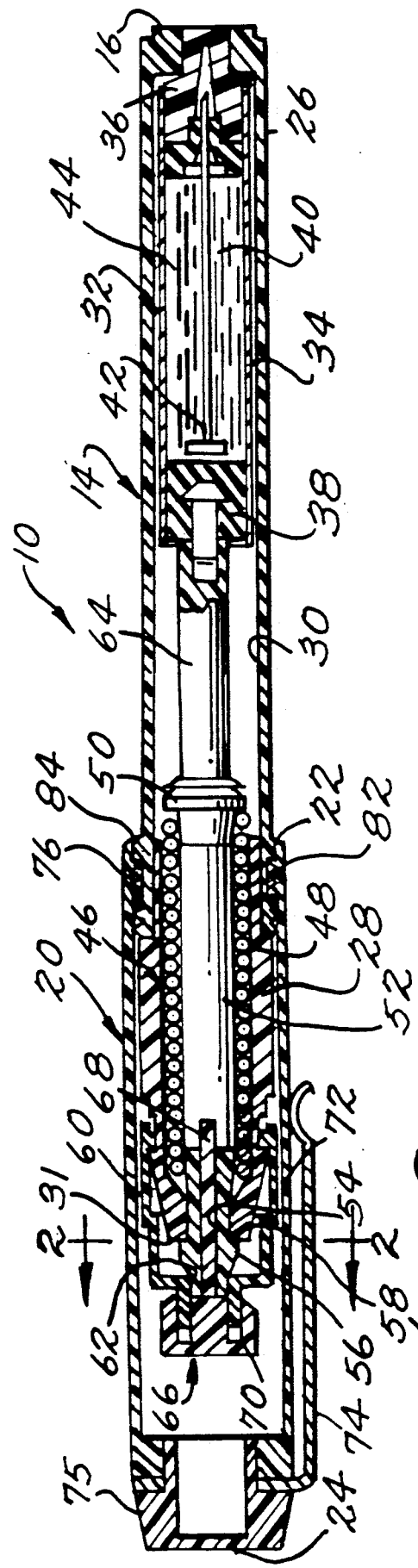
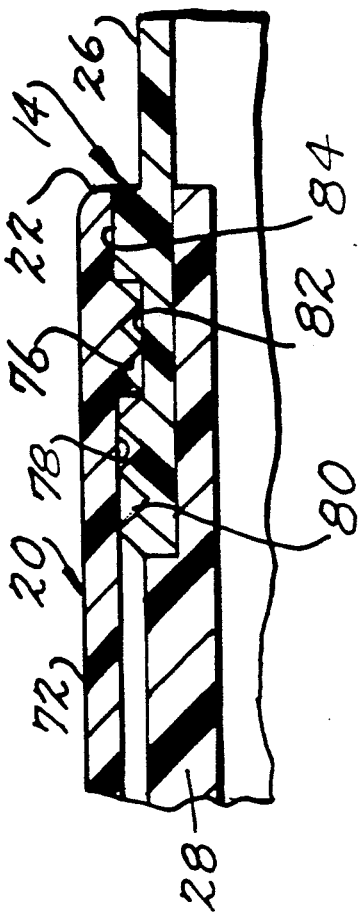
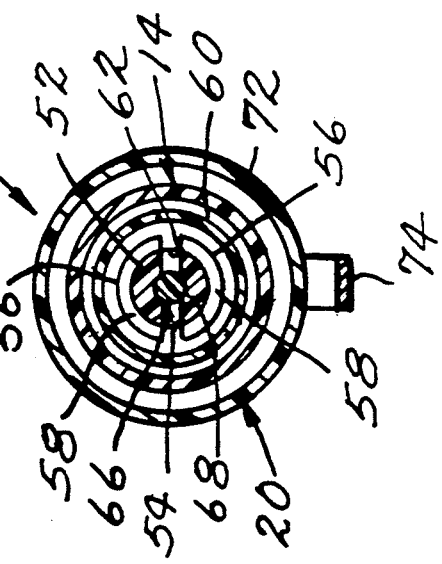

CONVENIENTLY CARRIED FREQUENT USE AUTOINJECTOR

This application relates to devices for injecting liquid medicaments and, more particularly, automatic injector types of such devices.

Automatic injectors are well known. Basically, an automatic injector is a device for enabling an individual to self-administer a dosage of a liquid medicament. An advantage of automatic injectors is that they contain a measured dosage of a liquid medicament in a sealed sterile condition capable of storage in such condition for an extensive period of non-use, during which period immediate injection of the stored dosage may be accomplished at any time under the most severe emergency conditions. Another advantage of automatic injectors is that the administration of the self-contained dosage of liquid medicament is accomplished without the necessity of the user initially seeing the hypodermic needle through which the liquid medicament is injected or of manually penetrating such a visible needle into the user's own tissue. Instead, an automatic injector includes a releasable stressed spring assembly. This assembly includes a stressed spring, a releasable mechanism for releasably retaining the spring in a stressed storage position and a releasing mechanism for releasing the releasable mechanism in response to a predetermined actuating procedure.

Automatic injectors have heretofore been particularly suited for use under emergency conditions. For example, many tens of millions of such automatic injectors have been manufactured and sold containing nerve gas antidotes for use under emergency chemical warfare conditions. Typical units which have been utilized for this purpose are disclosed in U.S. Pat. Nos. 2,832,339, 3,882,863, and 4,031,893. In addition, units of this type have been proposed for use in administering antiarrhythmic medicaments under emergency conditions relating to heart attack medical situations. Such use has been in conjunction with portable monitors as is evident from the disclosure contained in U.S. Pat. Nos. 3,910,260 and 4,004,577. It has also been proposed to provide other medicaments useful in treating heart attack symptoms such as clot selective thrombolytic agents (e.g. tPA) and related medicaments. See, for example, U.S. Pat. Nos. 4,689,042, 4,755,169, and 4,795,433. Finally, automatic injectors have been marketed in recent years containing a dosage of epinephrine as an antidote for counteracting severe allergic reactions, as for example, to bee stings and the like.

In all of these instances, the emergency use aspect of the automatic injectors is of primary significance.

The present invention stems from the recognition that the advantages of automatic injectors are not limited only to emergency situations but that there are many other medicinal administration situations requiring a much more frequent usage where the painlessness and simplicity of actuation of an automatic injector combined with other conveniences, would be sufficiently desirable to many individuals to warrant the added costs in comparison with the more simple and less costly manual syringes in widespread use. For example, recently the drug erythropoietin has been approved by the FDA in combating anemia. The drug is particularly useful to kidney patients, aids patients, and patients donating blood for their own use in anticipation of elective surgery. Such patients may have need for the administration of erythropoietin as frequently as once a week. An automatic injector provides a very convenient way of allowing the patient to administer the necessary erythropoietin without requiring the patient to become proficient in inserting a needle into his own flesh. Under circumstances of this type, it is desirable to provide the user with maximum convenience in availability, handling, and use of the automatic injector while at the same time discouraging use by others, particularly children.

Accordingly, it is an object of the present invention to provide an autoinjector particularly suited to be carried on the person of a user comprising an exterior housing of a size approximately the same as that of a conventional fountain pen. The exterior housing includes a housing body assembly of elongated generally cylindrical configuration having a needle extension end and an opposite end and a separate housing cap structure of elongated generally cylindrical configuration having an open end and an opposite closed end. The housing cap structure is detachably secured in open ended telescopic relation with the opposite end portion of the housing body assembly and has an elongated clip fixed at one of its ends in a position adjacent the closed end of the cap structure so as to extend longitudinally therealong. An opposite end of the clip is biased to engage with the exterior of the cap structure adjacent the open end thereof whereby the clip serves to secure the exterior housing within a pocket on the person of a user. The housing body assembly defines an interior chamber within which a medicament cartridge assembly is mounted in a storage position adjacent the needle extension end of the housing body assembly. The cartridge assembly includes a container, a liquid medicament within the container and a hypodermic needle disposed in a storage position and movable therefrom into an extended operative position. A releasable stressed spring assembly is also mounted in the interior chamber adjacent the opposite end of the housing body assembly. The spring assembly includes a spring, a releasable mechanism for retaining the spring in a stressed storage position and a releasing mechanism operable in response to a predetermined manual actuating procedure to release the releasable mechanism so that the spring moves (1) the hypodermic needle into the extended operative position thereof during which the hypodermic needle moves outwardly of the needle extension end of the housing body assembly through the skin and into the adjacent tissue of a user and (2) the liquid medicament outwardly through the hypodermic needle into the tissue of the user. The releasing mechanism includes a manually movable member extending from the opposite end of the housing body assembly into an exterior position suitable for manual engagement so as to be manually moved during the manual actuating procedure to which the releasing mechanism is responsive to release the releasable mechanism. The housing cap structure covers the manually movable member when the housing cap structure is secured to the housing body assembly so as to prevent the manual engagement of the manually movable member without the housing cap structure being detached from the housing body assembly thereby enabling the housing cap structure to serve the dual purposes of (1) facilitating the securement of the exterior housing with the user's pocket and (2) alleviating the likelihood of an unwanted release of the releasable member with a resultant unwanted movement of the hypodermic needle and an unwanted movement of the liquid medicament outwardly of the hypodermic needle.

Another object of the present invention is the provision of an autoinjector of the type described which is simple in construction, effective in operation and economical to manufacture.

These and other objects of the present invention will become more apparent during the course of the following detailed description and appended claims.

The invention may best be understood with reference to the accompanying drawings wherein illustrative embodiments are shown.

IN THE DRAWINGS:

FIG. 1 is a longitudinal sectional view of one embodiment of an automatic injector embodying the principles of the present invention;

FIG. 2 is an enlarged sectional view taken along the line 2—2 of FIG. 1;

FIG. 3 is an enlarged fragmentary sectional view of the portion of the injector encircled in FIG. 1.

Figure 4:
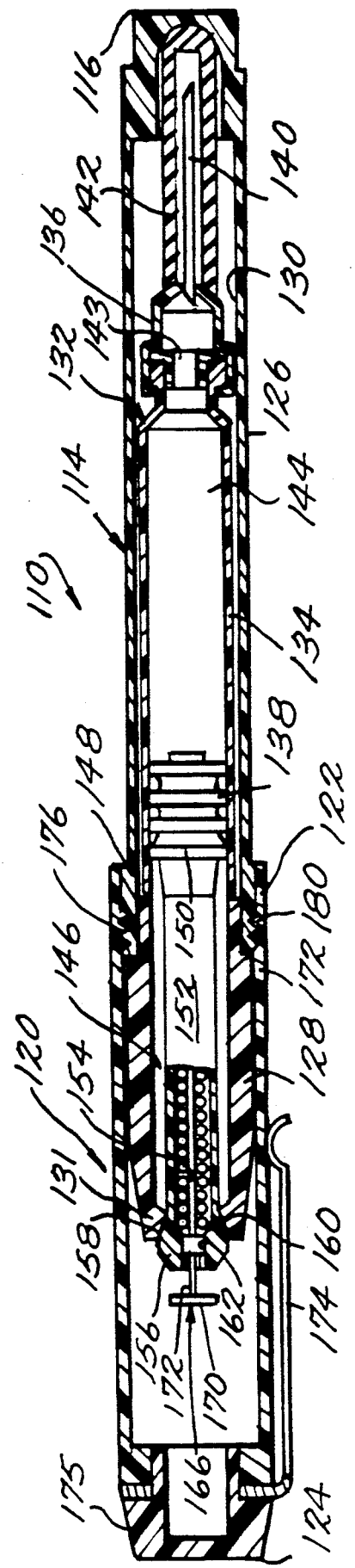
FIG. 4 is a view similar to FIG. 1 showing another embodiment of an autoinjector embodying the principles of the present invention.

Referring now more particularly to FIGS. 1 and 2 of the drawings, there is shown therein an autoinjector or automatic injector device, generally indicated at 10, which embodies the principles of the present invention. The autoinjector 10 presents an exterior configuration which is of a size approximately the same as that of a conventional fountain pen. The forward exterior is defined by a housing body assembly, generally indicated at 14, of elongated generally cylindrical configuration providing a forward needle extension end 16. The rearward exterior of the device is defined by a separate housing cap structure, generally indicated at 20, which is of elongated generally cylindrical configuration having an open end 22 and an opposite closed end 24.

The housing body assembly 14 includes two fixed forward and rearward tubular housing members 26 and 28, respectively. The forward housing member 26 is of greater length and provides the forward needle extension end 16 of the housing body assembly 14. The two fixed housing members together define an interior chamber 30 extending from the forward end 16 of the forward member 26 to a rearward end 31 of the rearward member 28. Mounted in a storage position within the needle extension end 16 of the chamber 30 provided by the forward housing member 26 is a medicament cartridge assembly, generally indicated at 32. The assembly 32 includes a generally cylindrical medicament container 34 having a forward end closed, as by an elastomeric stopper or plug assembly 36. A piston 38 closes the rearward end of the container 34 and is mounted therein for forward sliding movement in sealing relation with the interior of the container 34.

Mounted within the container 34 between the plug assembly 36 and the movable piston 38 is a hypodermic needle 40 having a forward sharpened end positioned within the plug assembly 36 and a rearward blunt disposed adjacent the piston 38. A lateral opening 42 is formed adjacent the blunt end of the needle 40 to provide communication through the hollow hypodermic needle 40 of a medicament 44 also stored within the container 34 between the plug assembly 36 and the piston 38. In accordance with conventional practice, the liquid medicament 44 does not completely fill the space defined by the container between the plug assembly 36 and the piston 38, but instead, there is an appropriate mount of air or other gas contained therein all in accordance with the teachings set forth in U.S. Pat. No. 3,396,726, the disclosure of which is hereby incorporated by reference into the present specification.

A stressed spring assembly, generally indicated at 46, is carried by the rearward housing member 28. It is preferable to assemble the components of the stressed spring assembly 26 with the rearward housing member 28 prior to the connection of the two housing members 26 and 28 together. Consequently, the housing member 28 is properly considered a part of the stressed spring assembly 46 as well as a part of the housing body assembly. In this regard, it will be noted that the forward end of the rearward housing member 28 is of reduced diameter so as to engage within the hollow rearward end of the forward housing member 26. The engagement preferably is fixed either by sonic welding adhesive, press fit or other means such as threads, etc.

The stressed spring assembly 46 includes a compression coil spring 48 within the chamber 30 which has one end engaged within the interior of the opposite end 31 provided by the rearward housing member 28. The opposite end of the spring 48 is stressed against an annular flange 50 formed on a forward end of a collet 52 which constitutes a releasable mechanism for retaining the spring 48 in stressed condition. The collet 52 may be of any conventional configuration; however, as shown, it is constructed of plastic material in the manner disclosed in U.S. Pat. No. 3,795,061, the disclosure of which is hereby incorporated by reference into the present specification. As shown, the collet is hollow and has its rearward end divided, as by a slot 54 into two flexible portions. Formed on the rearward end of the flexible portions are arcuate locking wedges 56 having forwardly facing locking surfaces 58 which engage the rearwardly facing annular surface provided by the opposite end 31 of the rearward housing member 28.

The stressed spring assembly 46 also includes a releasing mechanism which is in the form of a tubular releasing member 60. The releasing member 60, as shown, extends over the rearward end of the rearward housing member 28 and extends forwardly for a short distance in surrounding relation to the rearward housing member 28 so as to define a rearward portion of the exterior of the device when the cap structure 20 is removed. Accordingly, the member 60 may also be considered part of the housing assembly 14 as well as a part of the stressed spring assembly 46. In this regard, it is similar to the housing member 20 in that it too forms a part of both the housing assembly 14 and the stressed spring assembly. As shown, the releasing member 60 is mounted for movement between a rearward storage position and a forward actuating position. As shown, the forward end of the tubular releasing member 60 includes a flange or series of spaced projections extending around the interior periphery thereof for seating within an annular groove in the exterior periphery of the rearward housing member 28. The rearward end of the releasing member is of reduced diameter and engages around the cylindrical terminal end of the collet 52 when the releasing member 60 is in its storage position. The reduced end includes a forwardly facing annular surface 62 which is disposed to engage the rearwardly facing segmental frustoconical surfaces of the locking wedges 56.

It can be seen that when the releasing member 60 is moved from its storage position, as shown, forwardly into its actuating position, the forwardly facing annular surface 62 of the releasing member 60 will engage the segmental frustoconical surfaces of the locking wedges 56 causing the locking wedges 56 to move inwardly toward one another, thus moving the locking surfaces 58 of the wedges out of engagement with the rearward surface of the opposite end 31 of the rearward housing member 28, thus enabling the stressed spring 48 acting on the flange 50 of the collet 52 to move the collet 52 forwardly. Mounted between the flange of the collet 52 and the piston 38 of the medicament cartridge assembly 32 is an elongated spacer 64 so that as the collet 52 moves forwardly under the stress of the spring 48, piston 38 will be moved with the collet within the medicament container 34. During the initial part of this movement, the air in the container 34 is compressed and the sharpened end of the hypodermic needle 40 is moved outwardly through the plug assembly and the needle extension end 16 of the forward housing member 26 and into the tissue of the user. As the sharpened end of the needle 40 moves through the tissue of the user, the liquid medicament 44 within the container 30 is forced to flow into the opening 42 and out of the sharpened end of the hollow hypodermic needle 40 and into the tissue of the user.

The stressed spring assembly 46 also includes a safety, generally indicated at 66, which includes a forwardly extending safety pin 68 of a size to engage within the hollow interior of the rearward portion of the collet 52 so as to prevent the two locking wedges 66 to move toward one another. The safety also includes a cap 70 which, as shown, extends rearward from the rearward end of the housing body assembly defined by the releasing member 60. The cap is integrally interconnected with the safety pin 68 by a central enlargement which, in the safety storage position shown, extends within the reduced rearward end of the releasing member 60 in engagement with the end of the collet 52.

A feature of the present invention is that the housing cap structure 20 provides both a convenience to the user in carrying the autoinjector 0 on the person of the user and an added safety factor which prevents the stressed spring assembly 46 from being actuated without removing the housing cap structure 20. To this end, the housing cap 20 structure includes a tubular cap member 72 having fixed thereon a resilient clip 74. The clip 74, as shown, is of L-shaped configuration having one leg formed in a annular configuration so as to be fixed to the rearward end 24 of the housing cap structure 20. In this regard, it will be noted that the cap member 72 is an open ended tubular member and a closure 75 is provided to close the rearward open end thereof. The closure 75 includes a forwardly extending skirt which seats within the open end of the cap member 72 so as to capture the annularly shaped leg of the clip 74 therein. The other leg of the L-shaped clip 74 extends forwardly along the cap member 72 and has a knob formation on its forward extremity which is resiliently biased by the material of the clip 74 to engage the adjacent exterior periphery of the cap member 72. It will be understood that the construction of the cap structure 20 including the clip 74 and the manner of attaching the clip 74 are exemplary only and that other constructions and modes of assembly may be utilized if desired.

In accordance with the principles of the present invention, there is provided interengaging means between the cap structure 20 and the housing body assembly 14 for detachably securing the cap structure 20 in open ended telescopic relation with respect to the opposite end portion of the housing body assembly, as shown. While it is within the contemplation of the present invention in its broadest aspects to utilize any attaching means known for example in fountain pen technology, it is preferable to provide a means which requires for removal a combination of at least two different movements, either sequentially or simultaneously, so as to make the removal of the cap structure 20 from the housing body assembly 14 relatively difficult for children to accomplish. One embodiment of such a means is best shown in FIG. 3 as including a short section of threads 76 on the interior of the cap member adjacent the forward open end 22 thereof with a groove 78 formed inwardly adjacent the threaded section 76. Similarly, the exterior periphery of the rearward end of the rearward housing member 28 is formed with a cooperating exterior thread section 80 and an inwardly adjacent annular groove 82. As shown, a stop flange 84 is provided on the exterior of the housing member 26 so as to define the forward extremity of the groove 82 and capture the thread section 76 of the cap structure 20 therein when in attached relation. It can be seen that the cap structure 20 is attached by simply interengaging the threads 76 with the threads 80 and effecting a relative turning movement between the cap structure 20 and the housing body assembly 14. This turning movement will ultimately result in the interior thread section 76 engaging within the groove 82 and the exterior thread section 80 engaging within the groove 78, as best shown in FIG. 3. This interengagement serves to retain the cap structure 20 on the housing body assembly 14 in such a way that a simple relative turning movement between the cap structure and the body assembly will merely result in the two thread sections rotating within the grooves within which they are engaged. In order to remove the cap structure 20, it is necessary to apply a rearward pulling movement in addition to the turning movement to ensure that the thread sections 76 and 80 will initially interengage and then mesh throughout the turning action until they finally release to permit the cap structure 20 to be removed. It will be understood that other compound movements can be utilized such as a sequential push-in movement and then a turning movement.

The autoinjector as described above is particularly convenient to be carried on the person of a user in a manner similar to a conventional fountain pen. The exterior configuration of the device fits easily within the pocket and the clip 74 serves to retain the housing body assembly 14 and the cap structure 20 in the pocket on the person of the user. When it is desired to use the autoinjector, the user simply removes the autoinjector 10 from his pocket and utilizing the compound movements previously described removes the cap structure 20. This cap removal may be considered an initial step in a predetermined actuating procedure which must be accomplished in order to administer the medicament 44. The second step is to remove the safety 66 from its storage position by simply digitally gripping the cap 70 and pulling rearwardly with the housing body assembly gripped within the palm of one hand. Next, the thumb of the hand gripping the housing body assembly is extended over the rearward end portion of the releasing member 60. The needle extension end 16 of the housing member 26 is then brought into contact with the user's skin in the area where it is desired to effect the injection of the medicament. Once this contact has been established, the user simply presses his thumb down on the rearward end of the releasing member which has the effect of moving the locking wedges 56 inwardly towards one another, releasing the spring 48 and thus moving the needle 40 forwardly and into the tissue of the user and the medicament 44 within the container 34 outwardly through the needle 40 into the tissue of the user, all of which has been described in detail.

It will be understood that while the manual actuating procedure to effect actuation of the automatic injector 10 includes the removal of the safety and the pushing of the thumb against the rear end of the releasing member, the autoinjector can be made to be actuated in response to other specific actuating procedures. For example, many of the well-known existing automatic injectors simply utilize an actuating procedure in which actuation is effected by first removing the safety and then gripping the outer housing and pushing the outer housing forwardly so that the needle extension end engages the skin. This movement effects the release of the collet. This modification can be effected by extending the releasing member 60 forwardly over both of the housing members 26 and 28 so that it defines a substantial part of the exterior configuration of the device at all times not just when the cap structure is removed. Examples of actuations of this type are disclosed in U.S. Pat. No. 2,832,339, the disclosure of which is hereby incorporated by reference into the present specification. Moreover, since the cap serves as a safety, the invention in its broadest aspect contemplates elimination of the safety and its removal as a step in the predetermined actuating procedure required to effect injection.

Referring now more particularly to FIG. 4, there is shown therein another embodiment of an autoinjector, generally indicated at 110. Basically, the autoinjector 110 includes all of the components of the autoinjector 10 except that the medicament cartridge assembly 32 and spacer 64 are replaced by a different medicament cartridge assembly, generally indicated at 132, the stressed spring assembly 46 is replaced by a different stressed spring assembly 146 and the childproof connection between the housing body assembly 14 and the cap structure 20 is replaced by a conventional connection. Since the remaining components of the autoinjector are the same as previously described, these parts will not be specifically described and are given reference characters which are the same as before except for the addition of the prefix number 1 in front.

As shown, the medicament cartridge assembly 132 includes a medicament container 134 which is open at its rearward end and necked down at its forward end to receive a hub assembly 136. A piston 138 is mounted within the open rearward end of the container 134. The hub assembly 136 has fixed to the forward end thereof the rearward end of a hypodermic needle 140 which extends forwardly therefrom. The hypodermic needle and the hub structure is encased within a resilient sheath 142. Preferably, as shown, the hub assembly 136 is of the type Which includes a seal 143 in the rearward portion thereof such as disclosed in U.S. Pat. No. 3,380,449 and 3,391,695, the disclosures of which are hereby incorporated by reference into the present specification. The seal 143 of the hub assembly 136 serves to sealingly confine a liquid medicament 144 within the container 134 at its forward end with the piston 138 confining it at its rearward end. The operation and actuation of the autoinjector 110 is the same as the autoinjector 10 except that when the releasable collet 152 is released by the releasing member 150 after having removed the safety 166, the flange 150 of the collet 152 and released spring 148 act directly on the piston 138 in such a way as to move the entire medicament cartridge assembly 132 forwardly within the chamber 30 defined by the housing members 126 and 128. During this movement the sharpened forward end of the hypodermic needle 140 pierces the end of the sheath 142 and moves outwardly of the needle extension end 116 of the housing member 126 and into the tissue of the user. As this movement continues, the resilient sheath 136 is compressed so as to ultimately retard and stop the forward movement of the medicament container 134. When the medicament container 134 stops, the penetration of the needle within the user's tissue likewise stops but the piston 138 continues under the action of the spring to move forwardly causing the liquid medicament 144 to move from within the container 134 through the hypodermic needle 140 and into the tissue of the user. Cartridge assemblies of this type are well known as exemplified by U.S. Pat. No. 3,882,863 and the disclosure of which is hereby incorporated by references into the present specification.

The stressed spring assembly 146 is similar to the assembly 46 in that it includes the rearward housing member 128 within which is mounted a coil spring 148. The major difference between the stressed spring assembly 146 and the assembly 46 is that the former does not include a separate removable safety member 66. Instead, a single movement serves to disarm the safety and initiate actuation in the manner disclosed and claimed in U.S. Pat. No. 4,755,169, the disclosure of which is incorporated by reference into the present specification.

The compression coil spring 148 within the chamber 130 has a rearward end engaged within the interior of the opposite end 131 provided by the rearward housing member 128. The opposite forward end of the spring 148 is stressed against an annular flange 150 formed on a forward end of a collet 152 which constitutes a releasable mechanism for retaining the spring 148 in stressed condition. The collet 152, as shown, is hollow and has its rearward end portion divided, as by a slot 154, into two flexible fingers. Formed on the rearward end of the flexible fingers are arcuate locking wedges 156 having forwardly facing inclined locking surfaces 158 which engage a rearwardly facing frustoconical annular surface 160 provided on the opposite end 131 of the rearward housing member 128. In addition, the interior of the collet fingers are formed with inwardly projecting releasing surfaces 162.

Mounted within the interior of the releasing surfaces 162 of the collet fingers is a releasing mechanism, generally indicated at !66. The releasing mechanism 166 is of the type adapted to release the collet spring fingers either when moved forwardly or rearwardly with respect to the rear end of the associated collet spring fingers. Such a releasing action is possible because the locking surfaces 158 are inclined with respect to the annular surface 160 rather than being perpendicular thereto as is the case with locking surfaces 58. As shown, the releasing mechanism 166 is in the form of a movable member having a forward movement preventing portion 168 which has a diameter sufficient to engage with the interior collet releasing surfaces 162 so as to be disposed in engagement therewith when the collet is in its storage position. The movable releasing member also includes an actuating button 170 spaced rearwardly from the movement preventing portion 168 by a slender stem 172.

The predetermined actuating procedure includes in addition to the initial step of removing the cap structure 120, the simple additional step of moving the releasing member 166 forwardly by a manual thumb pressure on the actuating button 170 with the forward end 116 positioned in operative relation with respect to the skin at the injection site of the user. When the button 170 is moved forwardly to move the releasing member 166 out of its storage position into an actuating position, the movement preventing portion 168 is likewise moved from its storage position in engagement with releasing surfaces 162 to a forward position out of engagement with the releasing surfaces 162 with the stem 172 assuming a central position within the releasing surfaces 162. In this way the locking wedges 156 are now in a condition capable of being moved together. This movement is automatically effected by the stress in spring 148 due to the camming action of the inclined locking surfaces 158 with respect to the inclined annular surface 160. It will be noted that the releasing member 166 once moved inwardly is captured by the collet and moved forwardly with the collet 152 through the entire operative stroke thereof. As previously indicated, the operation of the medicament cartridge assembly 132 is sequential during the operative stroke of the collet 152 under the action of spring 148. That is, first, the entire assembly moves forwardly and then the piston 138 moves with respect to the container 134 causing the seal 143 to break and the liquid medicament to flow out of the container 134, through the needle 142 and into the tissue of the user.

Finally, it will be noted that the childproof dual motion thread and groove configuration of FIGS. 1 and 2 is replaced by a simple pair of meshing threads 176 and 178 on the cap structure 120 and forward housing member 126 respectively. With this construction, the cap structure 120 is removed simply by unscrewing the same by a simple turning movement. It will be understood that other types of conventional pen cap securements may be utilized or that the childproof type arrangement may be utilized as well. Similarly, the autoinjector 10 may be fitted with a stressed spring assembly 146 in lieu of the assembly 144 just as the autoinjector 110 may utilize a stressed spring assembly 46 in lieu of the assembly 146.

The autoinjector 10 is particularly desirable with relatively smaller dosages in which the liquid medicament 44 is compatible with the metal with forms the hypodermic needle 40. The autoinjector 110 is desirable where the dosage is larger and/or the liquid medicament 144 must be sealed from the metal of the hypodermic needle 140. An additional advantage of the autoinjector 110 is that the cartridge assembly 132 utilized therein is suitable for use with a digital actuator to form a prefilled syringe. Stated differently, by utilizing this type of cartridge assembly, two modes of delivery of the same cartridge assembly can be made in a highly efficient cost effective manner.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An autoinjector comprising housing means defining an exterior configuration of a size and shape approximately the same as that of a conventional fountain pen, said housing means including a housing body assembly of elongated generally cylindrical configuration having a needle extension end and an opposite end and a separate housing cap structure of elongated generally cylindrical configuration having an open end and an opposite closed end, means between said housing body assembly and said housing cap structure for detachably securing said separate housing cap structure in open ended telescopic relation with the opposite end portion of said housing body assembly, said housing body assembly defining an interior chamber, a medicament cartridge assembly mounted in a storage position within said interior chamber adjacent the needle extension end of said housing body assembly including a container, a liquid medicament within said container and a hypodermic needle disposed in a storage position and movable therefrom into an extended operative position, a releasable stressed spring assembly carried by said housing body assembly adjacent the opposite end thereof including spring means, releasable means for retaining said spring means in a stressed storage position within said chamber and releasing means operable in response to a predetermined manual actuating procedure to release said releasable means so that said spring means moves (1) said hypodermic needle into said extended operative position during which the hypodermic needle moves outwardly of the needle extension end of said housing body assembly through the skin and into the adjacent tissue of a user and (2) said liquid medicament outwardly through said hypodermic needle into the tissue of the user, said releasing means including manually movable means extending from the opposite end of said housing body assembly into an exterior position suitable for manual engagement so as to be manually moved during the manual actuating procedure to which said releasing means is responsive to release said releasable means, said manually movable means including a safety member mounted in said exterior position extending from the opposite end of said housing body assembly for manual removal from said exterior position, said safety member having means for (1) preventing said releasing means from releasing said releasable means when said safety member is in said exterior position and (2) enabling said releasing means to release said releasable means in response to said predetermined manual actuating procedure which includes an initial manual engagement of said safety member and removal thereof from said exterior position, said housing cap structure covering said safety member when said housing cap structure is secured to said housing body assembly so as to prevent the manual engagement of said safety member without said housing cap structure being detached from said housing body assembly.

2. An autoinjector as defined in claim 1 wherein said housing body assembly includes a forward housing member defining the needle extension end thereof, a rearward housing member fixed to said forward housing member, and a movable releasing member in telescoping relation with respect to said rearward housing member for limited movement from a storage position into an actuating position, said predetermined manual actuating procedure to which said releasing means is responsive to release said releasable means including a subsequent relative movement of said releasing member in telescoping relation with respect to said rearward housing member into said actuating position by manually moving the same toward said forward housing member while the needle extension end of said housing body assembly is retained in an operative position with the skin of the user at the location where the injection is to take place.

3. An autoinjector particularly suited to be carried on the person of a user comprising housing means defining an exterior configuration of a size and shape approximately the same as that of a conventional fountain pen, said housing means including a housing body assembly of elongated generally cylindrical configuration having a needle extension end and an opposite end and a separate housing cap structure of elongated generally cylindrical configuration having an one end and an opposite closed end, an elongated clip having one end fixed to the exterior of said cap structure adjacent the closed end thereof so as to extend longitudinally therealong and a free end biased to engage with the exterior of said cap structure adjacent the open end thereof whereby said clip serves to secure said cap structure within a pocket on the person of a user, means between said housing body assembly and said housing cap structure for detachably securing said separate housing cap structure in open ended telescopic relation with an opposite end portion of said housing body assembly so that the latter is secured together with said cap structure within such pocket by said clip, said housing body assembly defining an interior chamber, a medicament cartridge assembly mounted in a storage position within said interior chamber adjacent the needle extension end of said housing body assembly including a container, a liquid medicament within said container and a hypodermic needle disposed in a storage position and movable therefrom into an extended operative position, a releasable stressed spring assembly carried by said housing body assembly adjacent the opposite end thereof including spring means, releasable means for retaining said spring means in a stressed storage position within said chamber and releasing means operable in response to a predetermined manual actuating procedure to release said releasable means so that said spring means moves (1) said hypodermic needle into said extended operative position during which the hypodermic needle moves outwardly of the needle extension end of said housing body assembly through the skin and into the adjacent tissue of a user and (2) said liquid medicament outwardly through said hypodermic needle into the tissue of the user, said releasing means including manually movable means extending beyond the opposite end portion of said housing body assembly into an exterior position suitable for manual engagement so as to be manually moved during the manual actuating procedure to which said releasing means is responsive to release said releasable means, said housing cap structure covering said manually movable means when said housing cap structure is secured to said housing body assembly so as to prevent the manual engagement of said manually movable means without said housing cap structure being detached form said housing body assembly thereby enabling said housing cap structure to serve the dual purposes of (1) facilitating the securement of the housing cap structure and body assembly with the user's pocket and (2) alleviating the likelihood of an unwanted release of the releasable means with a resultant unwanted movement of said hypodermic needle and an unwanted movement of the liquid medicament outwardly of the hypodermic needle, said housing body assembly including a forward housing member defining the needle extension end thereof, a rearward housing member fixed to said forward housing member, and a movable tubular releasing member mounted in telescoping relation with respect to said rearward housing member for limited movement from a storage position into an actuating position, said predetermined manual actuating procedure to which said releasing means is responsive to release said releasable means including a relative movement of said releasing member in telescoping relation with respect to said rearward housing member into said actuating position by manually moving the same toward said forward housing member with a thumb while the needle extension end of said housing body assembly is retained in an operative position with the skin of the user at the location where the injection is to take place, said manually movable means including a safety member mounted in said exterior position extending from the opposite end of said housing body assembly for manual removal form said exterior position, said safety member having means for (1) preventing said movement of said tubular member toward said forward housing member when said safety member is in said exterior position and (2) enabling said movement of said tubular member toward said forward housing member when said safety member is removed from said exterior position, said predetermined manual actuating procedure including a manual gripping of said safety member and removal thereof from said exterior position prior to said movement of said tubular member toward said forward housing member.

4. An autoinjector as defined in claim 3 wherein said forward housing member defines a portion of said chamber containing said medicament cartridge assembly, said rearward housing member and said tubular member forming parts of said releasable stressed spring assembly, and means for securing a forward end portion of said rearward housing member with a rearward end portion of said forward housing member so as to retain the medicament cartridge assembly contained within the latter in cooperating relation with said releasable stressed spring assembly carried by said rearward housing member.

5. An autoinjector as defined in claim 4 wherein said releasable means comprises a collet member having a flanged forward end portion and a plurality of locking elements on a rearward end portion normally biased into a locking position and operable to be moved relatively toward one another against such bias into a releasing position, said locking elements including forwardly facing locking surfaces, said rearward housing member including rearwardly facing locking surface means disposed to be engaged by the forwardly facing locking surfaces of said locking elements when in said locking position, said spring means comprising a compression coil spring compressed between an interior rearwardly facing abutment surface on said rearward housing member and the flanged forward end portion of said collet, said releasing means comprising inclined surfaces on said locking elements and cooperating surface means on said tubular releasing member for engaging said inclined surfaces and moving said locking elements toward one another in response to the movement of said tubular releasing member from said storage position into said actuating position to thereby disengage the forwardly facing locking surfaces of said locking elements with said rearwardly facing locking surface means.

6. An autoinjector as defined in claim 5 wherein said tubular releasing member includes a hollow rearward end portion or reduced diameter disposed rearwardly of said rearward housing member adapted to be thumb engaged to effect movement of said tubular releasing member from said storage position to said actuating position.

7. An autoinjector as defined in claim 6 wherein said safety member includes a forwardly extending pin portion disposed through the rearward end portion of said releasing member and between the locking elements of said collet when in said storage position so as to prevent relative movement of said locking elements toward one another out of the storage position thereof.

8. An autoinjector as defined in claim 7 wherein said means for detachably securing said housing cap structure is operable to enable said housing cap structure to be manually detachable from secured relation with said housing body assembly only by the application of two different manual actions relatively therebetween.

9. An autoinjector as defined in claim 8 wherein the two manual actions enabling said housing cap structure to be manually detached from secured relation with said housing body assembly by said means for detachably securing said housing cap structure comprises a combination of (1) a relative longitudinal movement in a direction to move the housing cap structure and body assembly apart and (2) a relative turning movement.

10. An autoinjector as defined in claim 9 wherein said container is mounted within said chamber of said housing body assembly for retention in the storage position thereof wherein a forward end thereof is disposed at the needle extension end of said housing body assembly, said container having an elastomeric stopper at said forward end thereof and a piston slidably sealingly mounted within a rearward end portion thereof, said liquid medicament and said hypodermic needle being mounted within said container between said stopper and said piston when in said storage position, said piston being movable by said spring means from the storage position thereof to an extended position during which said hypodermic needle is moved through said stopper and into the tissue of the user and said liquid medicament is moved through said hypodermic needle into the tissue of the user.

11. An autoinjector as defined in claim 3 wherein said means for detachably securing said housing cap structure is operable to enable said housing cap structure to be manually detachable from secured relation with said housing body assembly only by the application of two different manual actions relatively therebetween.

12. An autoinjector as defined in claim 11, wherein the two manual actions enabling said housing cap structure to be manually detached from secured relation with said housing body assembly by said means for detachably securing said housing cap structure comprises a combination of (1) a relative longitudinal movement in a direction to move the housing cap structure and body assembly apart and (2) a relative turning movement.

13. An autoinjector particularly suited to be carried on the person of a user comprising
housing means defining an exterior configuration of a size and shape approximately the same as that of a conventional fountain pen, said housing means including a housing body assembly of elongated generally cylindrical configuration having a needle extension end and an opposite end and a separate housing cap structure of elongated generally cylindrical configuration having an open end and an opposite closed end,
an elongated clip having one end fixed to the exterior of said cap structure adjacent the closed end thereof so as to extend longitudinally therealong and a free end biased to engage with the exterior of said cap structure adjacent the open end thereof whereby said clip serves to secure said cap structure within a pocket on the person of a user,
means between said housing body assembly and said housing cap structure for detachably securing said separate housing cap structure in open ended telescopic relation with an opposite end portion of said housing body assembly so that the latter is secured together with said cap structure within such pocket by said clip,
said housing body assembly defining an interior chamber,
a medicament cartridge assembly mounted in a storage position within said interior chamber adjacent the needle extension end of said housing body assembly including a container, a liquid medicament within said container and a hypodermic needle disposed in a storage position and movable therefrom into an extended operative position,
a releasable stressed spring assembly carried by said housing body assembly adjacent the opposite end thereof including spring means, releasable means for retaining said spring means in a stressed storage position within said chamber and releasing means operable in response to a predetermined manual actuating procedure to release said releasable means so that said spring means moves (1) said hypodermic needle into said extended operative position during which the hypodermic needle moves outwardly of the needle extension end of said housing body assembly through the skin and into the adjacent tissue of a user and (2) said liquid medicament outwardly through said hypodermic needle into the tissue of the user, said releasing means including manually movable means extending beyond the opposite end portion of said housing body assembly into an exterior position suitable for manual engagement so as to be manually moved during the manual actuating procedure to which said releasing means is responsive to release said releasable means, said housing cap structure covering said manually movable means when said housing cap structure is secured to said housing body assembly so as to prevent the manual engagement of said manually movable means without said housing cap structure being detached from said housing body assembly thereby enabling said housing cap structure to serve the dual purposes of (1) facilitating the securement of the housing cap structure and body assembly with the user's pocket and (2) alleviating the likelihood of an unwanted release of the releasable means with a resultant unwanted movement of said hypodermic needle and an unwanted movement of the liquid medicament outwardly of the hypodermic needle, said housing body assembly including a forward housing member defining the needle extension end thereof and a rearward housing member fixed to said forward housing member, said manually movable means including a movable releasing member mounted for movement from a storage position into an actuating position, said predetermined manual actuating procedure to which said releasing means is responsive to release said releasable means including a relative movement of said releasing member with respect to said rearward housing member into said actuating position by manually moving the same toward said forward housing member with a thumb while the needle extension end of said housing body assembly is retained in an operative position with the skin of the user at the location where the injection is to take place, said forward housing member defines a portion of said chamber containing said medicament cartridge assembly, said rearward housing member forming part of said releasable stressed spring assembly, and means for securing a forward end portion of said rearward housing member with a rearward end portion of said forward housing member so as to retain the medicament cartridge assembly contained within the latter in cooperating relation with said releasable stressed spring assembly carried by said rearward housing member, said container being mounted within said chamber of said housing body assembly for movement from the storage position thereof into an extended position within said chamber of said housing body assembly, a hub assembly connecting a rearward end of said hypodermic needle with a forward end of said container for movement therewith, a resilient sheath extending over said hypodermic needle when said hypodermic needle is in the storage position thereof, said container having a piston slidably sealingly mounted in a rearward end portion thereof in engagement with the liquid medicament within said container operable to be moved by said spring means into an extended position during which (1) said container is moved into its extended position, (2) said hypodermic needle is moved with said container through said sheath and into the tissue of the user while said sheath is compressed within said chamber of said housing body assembly and (3) said liquid medicament is moved out of said hypodermic needle into the tissue of the user, said hub assembly having a seal therein normally sealing the liquid medicament from contact with said needle operable to burst in response to the initial portion of the movement of said piston within said container.

14. An autoinjector as defined in claim 13 wherein said releasable means comprises a collet member having a plurality of annularly spaced elongated fingers connected with the rearward end portion thereof for radially inward movement from a collet retaining position into a collet releasing position, said fingers having exterior collet retaining surfaces on outer portions thereof and interior collet releasing surfaces on inner portions thereof, cooperating collet retaining surface means on said rearward housing member engaging said exterior collet retaining surfaces for (1) retaining (a) said collet against forward movement and (b) said spring
means in stressed condition when said releasing member is in said storage position and (2) for enabling the stressed condition of said spring means to effect (a) radially inward movement of said fingers and (b) forward movement of said collet in response to the movement of said releasing member into said actuating position.

15. An autoinjector as defined in claim 14 wherein said releasing member includes (1) a forward portion having exterior surface means engaging said interior collet releasing surfaces when said releasing member is in said storage position, (2) a button portion spaced rearwardly of said forward portion for engagement by the thumb of the user, and (3) a slender stem portion connected between said forward portion and said button portion.

16. An autoinjector as defined in claim 13 wherein said means for detachably securing said housing cap structure is operable to enable said housing cap structure to be manually detachable from secured relation with said housing body assembly by the application of a simple manual turning movement relatively therebetween.

17. An autoinjector particularly suited to be carried on the person of a user comprising
housing means defining an exterior configuration of a size and shape approximately the same as that of a conventional fountain pen, said housing means including a housing body assembly of elongated generally cylindrical configuration having a needle extension end and an opposite end and a separate housing cap structure of elongated generally cylindrical configuration having an open end and an opposite closed end, an elongated clip having one end fixed to the exterior of said cap structure adjacent the closed end thereof so as to extend longitudinally therealong and a free end biased to engage with the exterior of said cap structure adjacent the open end thereof whereby said clip serves to secure said cap structure within a pocket on the person of a user, means between said housing body assembly and said housing cap structure for detachably securing said separate housing cap structure in open ended telescopic relation with an opposite end portion of said housing body assembly so that the latter is secured together with said cap structure within such pocket by said clip, said housing body assembly defining an interior chamber, a medicament cartridge assembly mounted in a storage position within said interior chamber adjacent the needle extension end of said housing body assembly including a container, a liquid medicament within said container and a hypodermic needle disposed in a storage position and movable therefrom into an extended operative position, a releasable stressed spring assembly carried by said housing body assembly adjacent the opposite end thereof including spring means, releasable means for retaining said spring means in a stressed storage position within said chamber and releasing means operable in response to a predetermined manual actuating procedure to release said releasable means so that said spring means moves (1) said hypodermic needle into said extended operative position during which the hypodermic needle moves outwardly of the needle extension end of said housing body assembly through the skin and into the adjacent tissue of a user and (2) said liquid medicament outwardly through said hypodermic needle into the tissue of the user, said releasing means including manually movable means extending beyond the opposite end portion of said housing body assembly into an exterior position suitable for manual engagement so as to be manually moved during the manual actuating procedure to which said releasing means is responsive to release said releasable means, said housing cap structure covering said manually movable means when said housing cap structure is secured to said housing body assembly so as to prevent the manual engagement of said manually movable means without said housing cap structure being detached from said housing body assembly thereby enabling said housing cap structure to serve the dual purposes of (1) facilitating the securement of the housing cap structure and body assembly with the user's pocket and (2) alleviating the likelihood of an unwanted release of the releasable means with a resultant unwanted movement of said hypodermic needle and an unwanted movement of the liquid medicament outwardly of the hypodermic needle, said container being mounted within said chamber of said housing body assembly for movement from the storage position thereof into an extended position within said chamber of said housing body assembly, said hypodermic needle being connected at a rearward end thereof with a forward end of said container for movement therewith, a resilient sheath extending over said hypodermic needle when said hypodermic needle is in the storage position thereof, said container having a piston slidably sealingly mounted in a rearward end portion thereof in engagement with the liquid medicament within said container operable to be moved by said spring means into an extended position during which (1) said container is moved into its extended position, (2) said hypodermic needle is moved with said container through said sheath and into the tissue of the user while said sheath is compressed within said chamber of said housing body assembly and (3) said liquid medicament is moved out of said hypodermic needle into the tissue of the user.

18. An autoinjector as defined in claim 17 wherein said manually movable means comprises a movable releasing member mounted for movement from a storage position into an actuating position, said releasable means comprises a collet member having a plurality of annularly spaced elongated fingers connected with the rearward end portion thereof for radially inward movement from a collet retaining position into a collet releasing position, said fingers having exterior collet retaining surfaces on outer portions thereof and interior collet releasing surfaces on inner portions thereof, cooperating collet retaining surface means on said rearward housing member engaging said exterior collet retaining surfaces for (1) retaining (a) said collet against forward movement and (b) said spring means in stressed condition when said releasing member is in said storage position and (2) for enabling the stressed condition of said spring means to effect (a) radially inward movement of said fingers and (b) forward movement of said collet in response to the movement of said releasing member into said actuating position.

19. An autoinjector as defined in claim 18 wherein said releasing member includes (1) a forward portion having exterior surface means engaging said interior collet releasing surfaces when said releasing member is in said storage position, (2) a button portion spaced rearwardly of said forward portion for engagement by the thumb of the user, and (3) a slender stem portion connected between said forward portion and said button portion.

20. An autoinjector as defined in claim 17 wherein said needle is connected with said container by a hub assembly having a seal therein normally sealing the liquid medicament from contact with said needle operable to burst in response to the initial portion of the movement of said piston within said container.

* * * * *